United States Patent
Yamamoto (10) Patent No.: US 10,639,010 B2
(45) Date of Patent: May 5, 2020

(54) PUNCTURE RANGE DETERMINATION APPARATUS AND METHOD

(71) Applicant: FUJIFILM Corporation, Tokyo (JP)

(72) Inventor: Hiroaki Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 417 days.

(21) Appl. No.: 15/634,026

(22) Filed: Jun. 27, 2017

(65) Prior Publication Data

US 2017/0290570 A1    Oct. 12, 2017

Related U.S. Application Data

(63) Continuation of application No. PCT/JP2016/053631, filed on Feb. 8, 2016.

(30) Foreign Application Priority Data

Mar. 12, 2015  (JP) .................. 2015-049821

(51) Int. Cl.
*A61B 8/00* (2006.01)
*A61B 8/14* (2006.01)
(Continued)

(52) U.S. Cl.
CPC .............. *A61B 8/463* (2013.01); *A61B 8/06* (2013.01); *A61B 8/08* (2013.01); *A61B 8/0891* (2013.01);
(Continued)

(58) Field of Classification Search
CPC .... A61B 8/06; A61B 8/08; A61B 8/14; A61B 8/0891; A61B 8/485; A61B 8/488; A61B 8/463; A61B 17/3403; A61B 2017/3413
See application file for complete search history.

(56) References Cited

U.S. PATENT DOCUMENTS

2009/0124903 A1    5/2009  Osaka
2014/0039316 A1*   2/2014  Ichioka ............... A61B 8/0841
                                                  600/439

FOREIGN PATENT DOCUMENTS

JP    2004-298476 A    10/2004
JP    2006-255015 A     9/2006
(Continued)

OTHER PUBLICATIONS

International Search Report, issued in PCT/JP2016/05361, dated Apr. 26, 2016.
(Continued)

*Primary Examiner* — Bo Joseph Peng (74) *Attorney, Agent, or Firm* — Birch, Stewart, Kolasch & Birch, LLP (57) ABSTRACT

Provided are a puncture range determination apparatus and a puncture range determination method in which the hardness of tissue is considered as well as blood vessels. A blood vessel (32) is detected through performing Doppler processing. In addition, a soft region (33) of a subject is detected through performing elastication processing. A range of the soft region (33) excluding the blood vessel (32) is detected as a puncture recommendation range. Guide lines (34) and (35) defining the puncture recommendation range are displayed. A doctor performs puncturing with a needle inside the guide lines (34) and (35) and punctures a puncture target region (31) with the needle.

13 Claims, 12 Drawing Sheets

(51) Int. Cl.
- *A61B 8/06* (2006.01)
- *A61B 8/08* (2006.01)
- *A61B 17/34* (2006.01)

(52) U.S. Cl.
CPC ............... *A61B 8/14* (2013.01); *A61B 8/485* (2013.01); *A61B 8/488* (2013.01); *A61B 17/3403* (2013.01); *A61B 2017/3413* (2013.01)

(56) References Cited

FOREIGN PATENT DOCUMENTS

| | | |
|---|---|---|
| JP | 2013-116263 A | 6/2013 |
| WO | 2006/054635 A1 | 5/2006 |

OTHER PUBLICATIONS

Written Opinion of the International Searching Authority, issued in PCT/JP2016/053631, dated Apr. 26, 2016.

* cited by examiner

PUNCTURE RANGE DETERMINATION APPARATUS AND METHOD

CROSS-REFERENCE TO RELATED APPLICATIONS

This application is a Continuation of PCT International Application No. PCT/JP2016/053631 filed on Feb. 8, 2016, which claims priority under 35 U.S.C. § 119(a) to Japanese Patent Application No. 2015-049821 filed Mar. 12, 2015. Each of the above application(s) is hereby expressly incorporated by reference, in its entirety, into the present application.

BACKGROUND OF THE INVENTION

1. Field of the Invention

The present invention relates to a puncture range determination apparatus and a puncture range determination method.

2. Description of the Related Art

In ultrasound-guided anesthesia using an ultrasound apparatus for a body surface or in puncture suction cytology in ultrasound endoscope, a procedure is performed while projecting a puncture needle on an ultrasound image. In some cases, if a blood vessel or the like of a subject is accidentally punctured with a needle, this would cause serious bleeding. For this reason, puncturing is performed while checking that there is no blood vessel on a puncture route after switching the image to a Doppler image. There is a method for extracting a region having no blood vessel from a Doppler image and displaying a guide line for puncturing is automatically displayed on the extracted region (JP2004-298476A).

SUMMARY OF THE INVENTION

However, in the method of JP2004-298476A, even if a puncture route having no blood vessel is selected from a Doppler image, in a case where a region with hard tissue is set to a puncture route, in some cases, the hard region is punctured with a needle, which causes bending of the needle. In addition, there is a concern that the needle may be deviated from the puncture route due to the bending of the needle, thereby damaging blood vessels.

An object of the present invention is to provide an appropriate puncture route while considering the hardness of tissue as well as considering blood vessels.

A puncture range determination apparatus according to the present invention comprises: an acoustic wave probe which outputs an acoustic wave echo signal by transmitting an acoustic wave to a subject and receiving an acoustic wave echo from the subject; a first detection device (first detection means) for detecting a first region having a fluid in the inside of the subject by performing Doppler processing using the acoustic wave echo signal output from the acoustic wave probe; a second detection device (second detection means) for detecting a second region of which the degree of softness in the inside of the subject is greater than or equal to a threshold value by performing an elastication processing using the acoustic wave echo signal output from the acoustic wave probe; and a puncture recommendation range determination device (puncture recommendation range determination means) for determining a range which includes the second region but excludes the first region, as a puncture recommendation range.

The present invention also provides a puncture range determination method. That is, the method comprises: causing a first detection device to detect a first region having a fluid in the inside of the subject by performing Doppler processing using an acoustic wave echo signal output from an acoustic wave probe which outputs an acoustic wave echo signal by transmitting an acoustic wave to a subject and receiving an acoustic wave echo from the subject; causing a second detection device to detect a second region of which the degree of softness in the inside of the subject is greater than or equal to a threshold value by performing elastication processing using the acoustic wave echo signal output from the acoustic wave probe; and causing a puncture recommendation range determination device to determine a range which includes the second region but excludes the first region, as a puncture recommendation range.

The puncture range determination apparatus may further include a third detection device (third detection means) for performing processing of detecting a non-echo region as a third region on a region excluding the first region in the inside of the subject using the acoustic wave echo signal output from the acoustic wave probe. In this case, the puncture recommendation range determination device determines, for example, at least one of a range including the second region but excluding the first region and a range including the third region but excluding the first region, as a puncture recommendation range.

The puncture recommendation range determination device may determine a range including the second region and the third region but excluding the first region, as a puncture recommendation range.

The second detection device may detect, for example, the second region by performing elastication processing on a region excluding the first region.

The third detection device may detect the third region by performing processing of detecting a non-echo region on a region excluding the first region and a region excluding the second region.

The puncture range determination apparatus may further comprise: an acoustic wave image generation device (acoustic wave image generation means) for generating an acoustic wave image in the inside of the subject using the acoustic wave echo signal output from the acoustic wave probe; and a first display control device (first display control means) which displays the puncture recommendation range on a display screen while superimposing the puncture recommendation range on the acoustic wave image.

The first display control device may display the puncture recommendation range in a color different from any of a color of the other range and a color of an image of a needle.

In a case where the puncture range determination apparatus further comprises an acoustic wave image generation device (acoustic wave image generation means) for generating an acoustic wave image in the inside of the subject using the acoustic wave echo signal output from the acoustic wave probe, the third detection device detects, for example, a region in which a liquid stays inside the subject using the acoustic wave image generated by the acoustic wave image generation device.

The puncture range determination apparatus may further comprise: a puncture target-setting device (puncture target-setting means) for setting a puncture target using the acoustic wave image; a shortest route determination device (shortest route determination means) for determining a shortest route up to the puncture target in a case where the puncture target is set and the puncture recommendation range is determined; and a second display control device (second display control means) for displaying the shortest route on a display screen.

The puncture range determination apparatus may further comprise: an acoustic wave image generation device (acoustic wave image generation means) for generating an acoustic wave image in the inside of the subject using the acoustic wave echo signal output from the acoustic wave probe; a third display control device (third display control means) for displaying a range including a region excluding the first region on a display screen as a puncturable range while superimposing the range containing the region excluding the first region on the acoustic wave image generated by the acoustic wave image generation device; and a detection command input device (detection command input means) for inputting a detection command for starting detection of the second region performed by the second detection device. In this case, the second detection device detects, for example, the second region in a case where the detection command is input to the detection command input device.

The first detection device may detect, for example, the first region by detecting a region excluding a fluid in the inside of the subject using the acoustic wave echo signal output from the acoustic wave probe.

The second detection device may detect, for example, a region of which the degree of hardness in the inside of the subject is less than the threshold value using the acoustic wave echo signal output from the acoustic wave probe to detect a region excluding the detected region, as the second region.

According to the present invention, a first region having a fluid in the inside of a subject is detected by performing Doppler processing using an acoustic wave echo signal output from an acoustic wave probe and a second region of which the degree of softness in the inside of the subject is greater than or equal to a threshold value is detected by performing elastication processing. A range including the second region but excluding the first region is determined as a puncture recommendation range. In the puncture recommendation range determined in this manner, it is possible to avoid a fluid region such as a blood stream and to prevent puncturing of blood vessels with a needle or bending of a needle due to puncturing a hard region even if the puncture recommendation range is punctured since the puncture recommendation range is a soft region so as not to cause bending of the needle.

DESCRIPTION OF THE PREFERRED EMBODIMENTS

Figure 1:
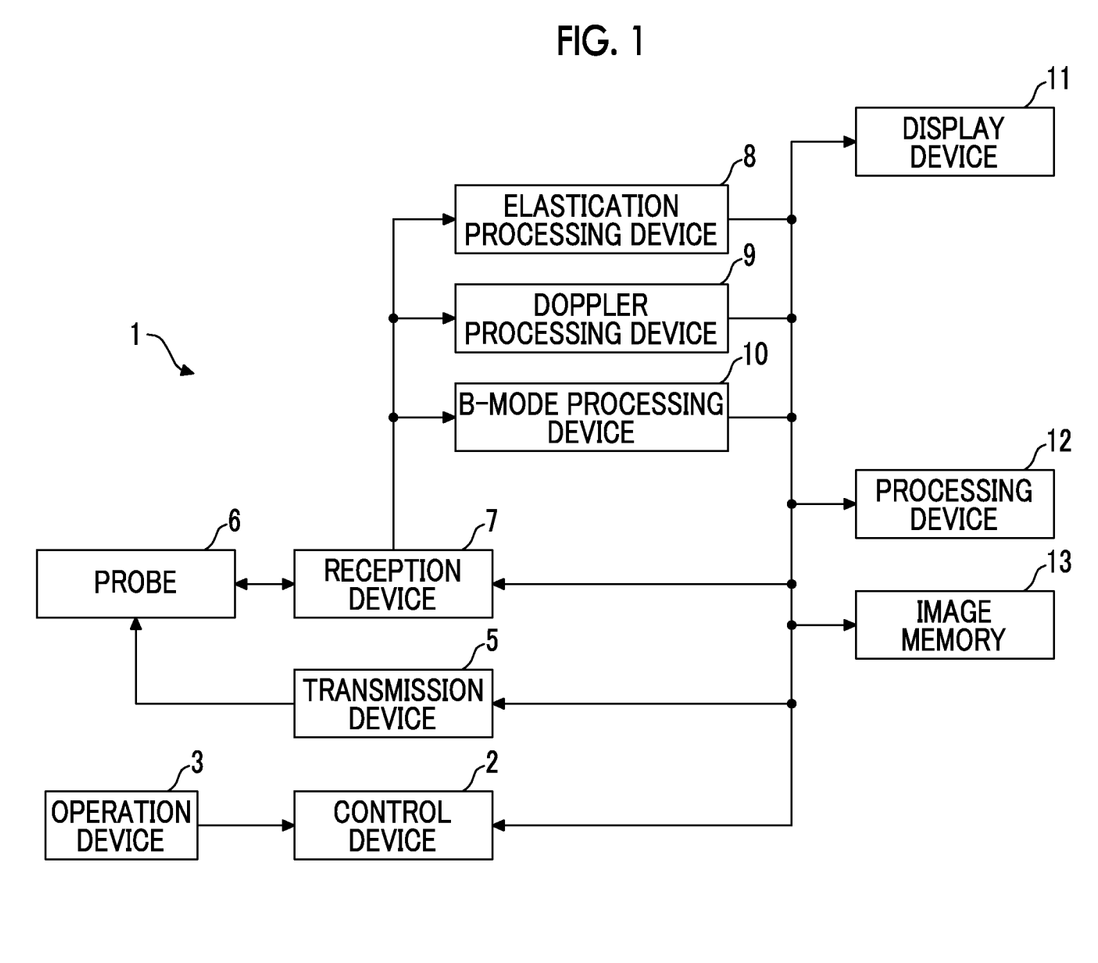
FIG. 1 is a block diagram showing an electrical configuration of an ultrasound diagnostic apparatus.

FIG. 1 is a block diagram which shows an example of the present invention and shows an electrical configuration of an ultrasound diagnostic apparatus (puncture range determination apparatus) 1.

In this example, an ultrasonic wave is used as an acoustic wave. However, the present invention is not limited to the ultrasonic wave and an audible frequency acoustic wave may be used as long as an appropriate frequency is selected in accordance with a test target, measurement conditions, and the like.

An overall operation of the ultrasound diagnostic apparatus 1 is controlled by a control device 2.

An operation device 3 which is operated by a doctor who operates the ultrasound diagnostic apparatus 1 is connected to the control device 2.

An ultrasound probe 6 (acoustic wave probe) is included in the ultrasound diagnostic apparatus 1. A plurality of ultrasound transducers (acoustic wave transducers) are included in the ultrasound probe 6.

A control signal output from the control device 2 is given to a transmission device 5. Then, an electric pulse is given to the ultrasound transducers of the ultrasound probe 6 from the transmission device 5. The ultrasound transducers are driven by the transmission device 5. The electric pulse is converted into an ultrasound pulse (ultrasonic wave) by the ultrasound transducers, the ultrasound pulse is propagated into the body of a subject, and an ultrasound echo is received in the ultrasound probe 6.

The ultrasound echo is output after being converted into an electric signal (ultrasound echo signal) in the ultrasound transducers. In this manner, the ultrasound echo signal is output by transmitting an ultrasonic wave to the subject and receiving an ultrasound echo from the subject using the ultrasound probe 6. The ultrasound echo signal is given to a reception device 7. Amplification of the ultrasound echo signal and analog/digital conversion are performed in the reception device 7 and the signal is converted into digital ultrasound echo data. The reception device 7 also includes a memory. The converted ultrasound echo data is temporarily stored in the memory.

The ultrasound diagnostic apparatus 1 according to this example include an elastication processing device 8, a Doppler processing device 9, and a B-mode processing device 10. The elastication processing device 8 (the second detection device) performs elastication processing using the ultrasound echo data stored in the memory of the reception device 7. A hard region in the inside of the subject is detected through the elastication processing (in other words, a soft region of which the degree of softness is greater than or equal to a threshold value is detected). The Doppler processing device 9 (the first detection device) performs Doppler processing using the ultrasound echo data stored in the memory of the reception device 7. A region having a fluid (region with movement) inside the subject is detected through the Doppler processing. Needless to say, in a case where the Doppler processing is performed, ultrasonic waves are transmitted to the same part of the subject a plurality of times and ultrasound echo data obtained based on ultrasound echoes obtained through the plurality of times of transmission of ultrasonic waves from the subject. The B-mode processing device 10 (the third detection device, acoustic the wave image generation device) performs processing of generating a B-mode image using ultrasound echo data stored in the memory of the reception device 7.

When output data of the elastication processing device 8 is given to a processing device 12, predetermined conversion processing or the like performed for display on a display device 11 is performed in the processing device 12, and an elastication image (an image in which the hardness and the softness of the inside of a subject is visualized) is displayed on a display screen of the display device 11 based on the control of the processing device 12. In addition, when output data of the Doppler processing device 9 is given to the processing device 12, predetermined conversion processing or the like performed for display on the display device 11 is performed in the processing device 12, and a Doppler image (an image in which a fluid in the inside of a subject or the speed of movement of a movable object is visualized) is displayed on the display screen of the display device 11 based on the control of the processing device 12. Furthermore, when output data of the B-mode image is given to the processing device 12, predetermined conversion processing or the like performed for display on the display device 11 is performed in the processing device 12, and the B-mode image is displayed on the display screen of the display device 11 based on the control of the processing device 12. Needless to say, not only one of the elastication image, the Doppler image, or the B-mode image is displayed on the display screen of the display device 11, but two or more images among the elastication image, the Doppler image, and the B-mode image may be displayed in a superimposed manner. In addition, needless to say, it is possible to display an image showing a soft region obtained in the elastication processing and an image showing a first region having a fluid (region with movement) obtained in the Doppler processing on the B-mode image in a superimposed manner using the processing device 12. In the method for displaying images in a superimposed manner, the images may be resultingly displayed in a state of being superimposed. One specific method is a method for synthesizing images. Another specific method is a method for displaying images by superimposing the images as separate layers.

In addition, the output data pieces of the elastication processing device 8, the Doppler processing device 9, and the B-mode processing device 10 are given to an image memory 13 and are temporarily stored therein. Any one of the elastication image, the Doppler image, and the B-mode image is displayed on the display screen of the display device 11 through reading of predetermined data from the data pieces stored in the image memory 13. Needless to say, even in a case where the data stored in the image memory 13 is read, it is possible to display two or more images among the elastication image, the Doppler image, and the B-mode image on the display screen of the display device 11 in a superimposed manner by reading two or more types of data pieces from the image memory 13.

Figure 2:
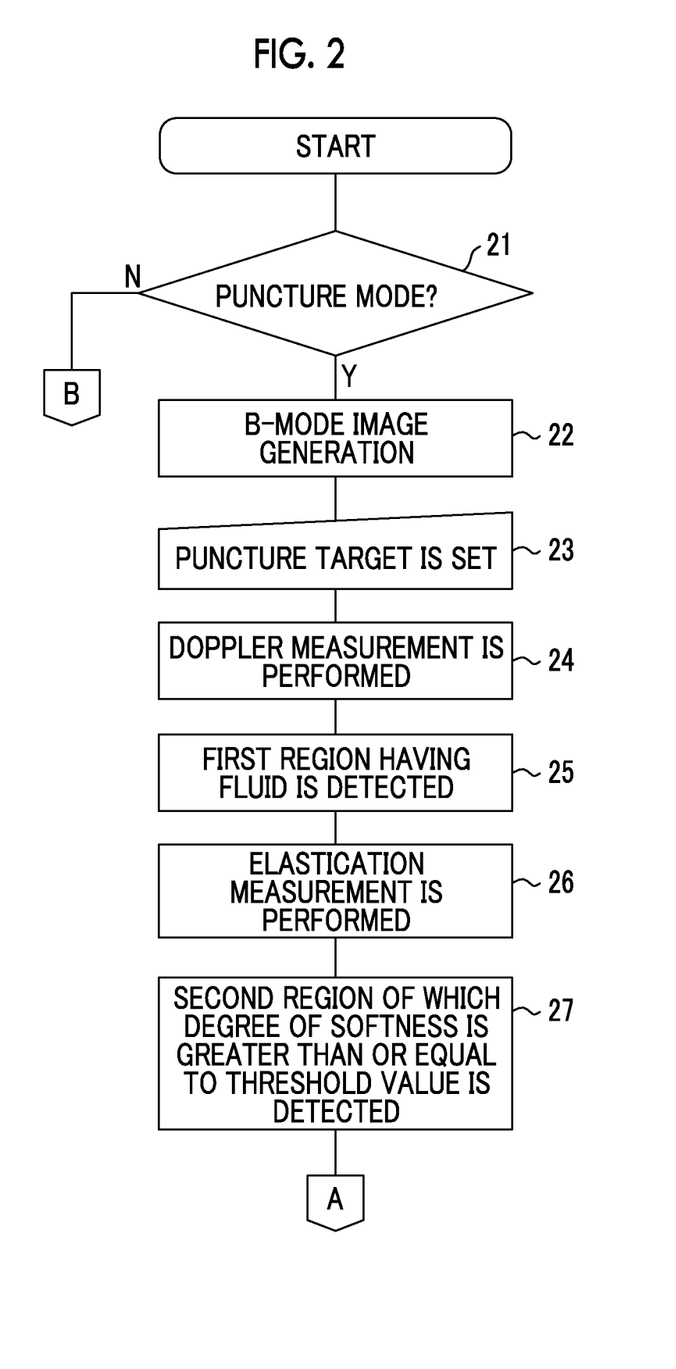
FIG. 2 is a flowchart showing a part of a processing procedure of the ultrasound diagnostic apparatus.
Figure 3:
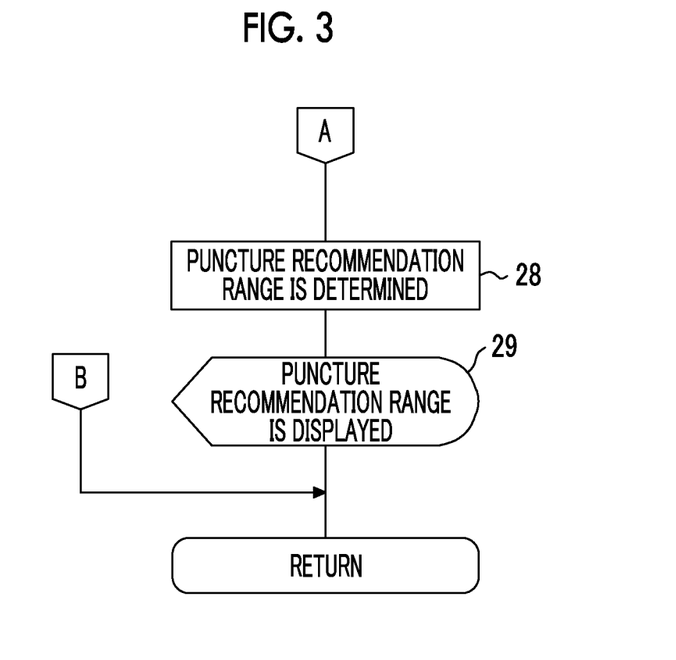
FIG. 3 is a flowchart showing a part of a processing procedure of the ultrasound diagnostic apparatus.

FIGS. 2 and 3 are flowcharts showing processing procedures of the ultrasound diagnostic apparatus 1.

In the ultrasound diagnostic apparatus 1 according to this example, it is possible to puncture a subject with a needle and to take out tissue to be punctured in the inside of the subject using the needle which has been used for the puncturing. The taken out tissue is inspected. Particularly, in this example, a range (a possible range as a range of performing puncturing with a needle) which is preferable as the range of performing the puncturing with the needle in the inside of the subject is displayed as a puncture recommendation range. A doctor punctures the subject while referring to the puncture recommendation range.

In a case of performing puncturing on a subject, a doctor sets a puncture mode using the operation device 3 (YES in step 21). An ultrasonic wave is transmitted to the subject from the ultrasound probe 6 and a B-mode image is generated in the B-mode processing device 10 as described above (step 22). When the generated B-mode image is displayed on the display screen of the display device 11, the doctor sets a puncture target in the inside of the subject using the operation device 3 (the puncture target-setting device) (step 23).

Figure 4:
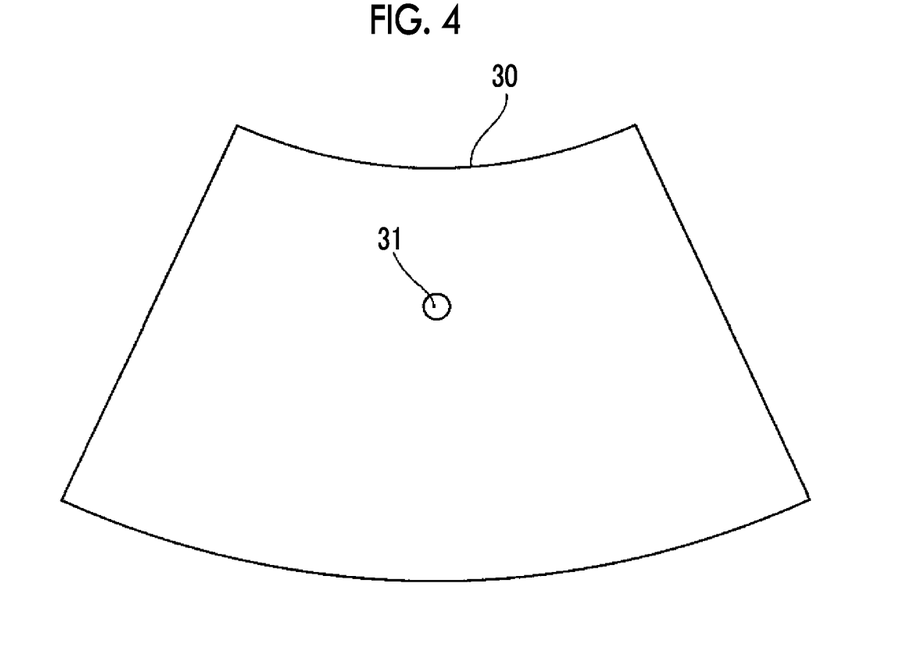
FIG. 4 is an example of an ultrasound image.

FIG. 4 is an example of an ultrasound image (B-mode image) 30 displayed on the display screen of the display device 11.

When the ultrasound image 30 is displayed on the display screen of the display device 11 as described above, the doctor sets a puncture target while checking the ultrasound image 30. A puncture target region 31 which has been set is displayed on the ultrasound image 30 according to the setting of the puncture target. The doctor moves a needle so as to puncture the puncture target region 31.

Returning to FIG. 2, subsequently, Doppler measurement (Doppler processing) is performed in the Doppler processing device 9 (step 24), and a first region having a fluid (region with movement) inside the subject is detected using the ultrasound echo signal output from the ultrasound probe 6, using the control device 2 (the first detection device) (step 25). It is possible to detect blood stream in the inside of the subject and the position of blood vessels through this Doppler processing.

Figure 5:
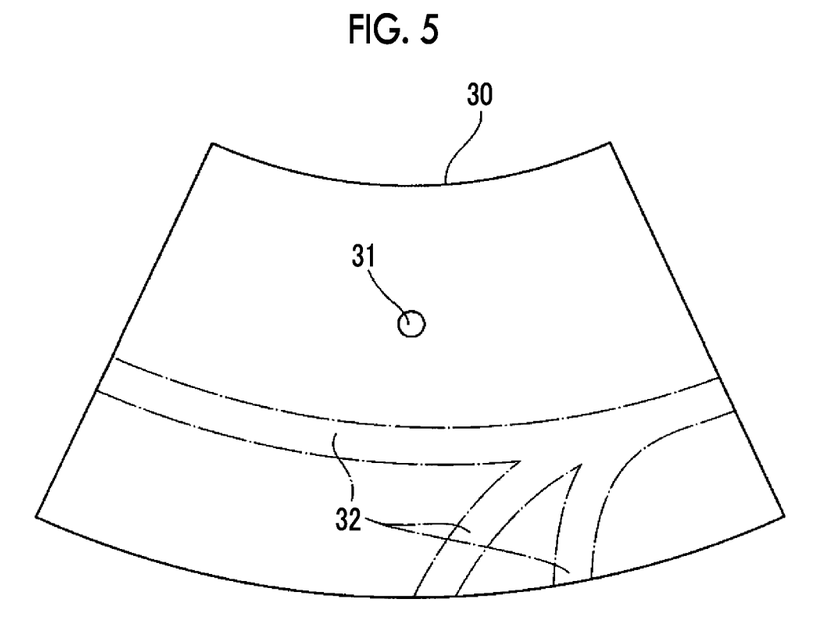
FIG. 5 is an example of an ultrasound image.

FIG. 5 is an example of the ultrasound image 30.

As described above, when the Doppler processing is performed, a blood stream 32 (first region having a fluid) is detected. The detected blood stream 32 is superimposed on the ultrasound image 30 generated in the B-mode processing device 10, using the processing device 12. In the method for displaying images in a superimposed manner, the images may be resultingly displayed in a state of being superimposed. One specific method is a method for synthesizing images to display the synthesized images as one image. Another specific method is a method for displaying images by superimposing the images as separate layers.

Returning to FIG. 2, elastication measurement (elastication processing) is performed in the elastication processing device 8 (step 26). In this elastication processing, a soft region (second region) of which the degree of softness is greater than or equal to a threshold value [data of the threshold value is stored in a memory (not shown in the drawing) of the ultrasound diagnostic apparatus 1] in the inside of the subject is detected in the control device 2 (the second detection device) using the ultrasound echo signal output from the ultrasound probe 6 (step 27). In general, it is known that elastography is displayed by relative hardness within a region of interest. However, the threshold value may be determined based on distortion or elastic modulus obtained in the subject or in the region of interest. For example, an average value of the distortion or the elastic modulus in the subject or in the region of interest may be set to a threshold value.

Figure 6:
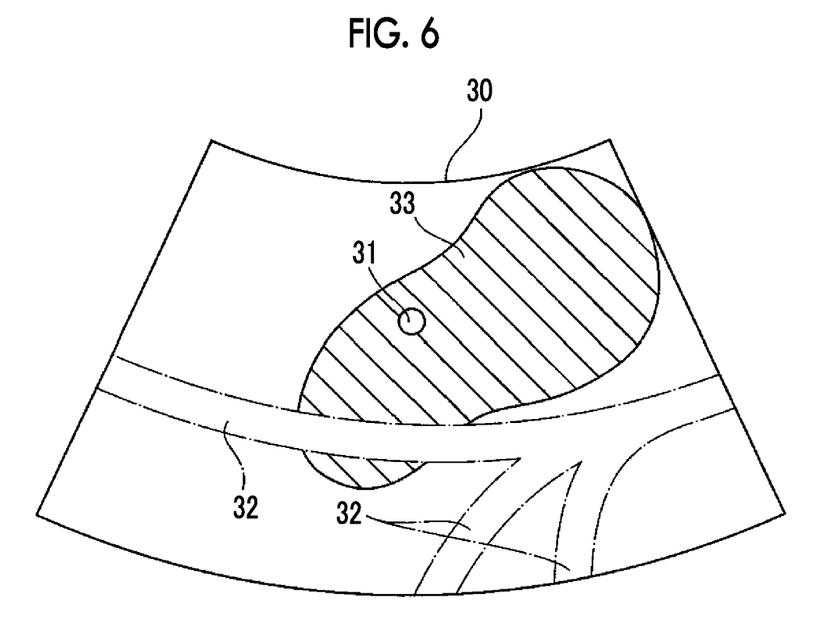
FIG. 6 is an example of an ultrasound image.

FIG. 6 is an example of the ultrasound image 30.

A soft region 33 of which the degree of softness is greater than or equal to a threshold value is detected by the control device 2 through elastication processing performed as described above. An image showing the detected soft region 33 is superimposed on the ultrasound image 30 by the processing device 12. In the method for displaying images in a superimposed manner, the images may be resultingly displayed in a state of being superimposed. One specific method is a method for synthesizing images to display the synthesized images as one image. Another specific method is a method for displaying images by superimposing the images as separate layers.

Referring to FIG. 3, when the blood stream 32 (the first region having a fluid) and the soft region 33 (the second region of which the degree of softness is greater than or equal to a threshold value) are detected by the control device 2, a puncture recommendation range is determined by the control device 2 (the puncture recommendation range determination device) (step 28). The puncture recommendation range is a range including the detected second region as a soft region but excluding the detected first region having a fluid.

Figure 7:
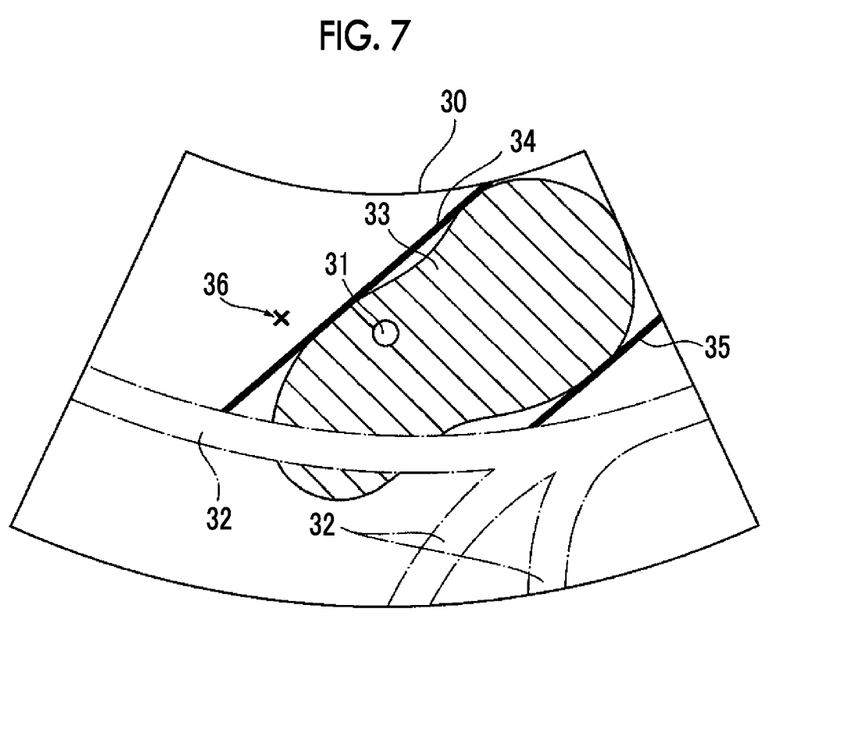
FIG. 7 is an example of an ultrasound image.

FIG. 7 is an example of the ultrasound image 30.

Referring to FIG. 7, the puncture recommendation range is a region excluding the region (the first region having a fluid) of the blood stream 32 and a region including the soft region 33 (second region). The puncture recommendation range is a range which is interposed between guide lines 34 and 35 in the ultrasound image 30. An area up to distal ends of the guide lines 34 and 35 is recommended as an area to be punctured. The range interposed between the guide lines in this manner is displayed on the display screen of the display device 11 by being superimposed on the ultrasound image as a puncture recommendation range, using the processing device 12 (the first display control device) (STEP 29). In the method for displaying images in a superimposed manner, the ultrasound image and the puncture recommendation range may be resultingly displayed in a state of being superimposed. One specific method is a method for synthesizing ultrasound image and the puncture recommendation range to display the ultrasound image and the puncture recommendation range as one image. Another specific method is a method for displaying ultrasound image and the puncture recommendation range by superimposing the ultrasound image and the puncture recommendation range as separate layers. The doctor performs puncturing with a needle within the puncture recommendation range such that the needle reaches the puncture target region 31. Since there is no blood stream 32 within the puncture recommendation range, it is possible to prevent blood vessels from being accidently punctured with the needle in advance. Furthermore, since there is no hard region in the puncture recommendation range, there is no concern that the needle may be bent. Furthermore, it is possible to prevent blood vessels from being accidently punctured with the needle in advance due to the bending of the needle. However, in a case where the puncture target exists outside the puncture recommendation range like a region shown by a reference numeral 36, the puncture target region 36 will be punctured even if the puncture target region is outside the puncture recommendation range. In a case where the puncture target exists outside the puncture recommendation range, a hard needle, which is hardly bent even if the hard region is punctured, will be used.

The display of the guide lines 34 and 35 refers to display of the puncture recommendation range. However, the range interposed between the guide lines 34 and 35 may be displayed in a superimposed manner (display of the puncture recommendation range) on the ultrasound image (acoustic wave image) 30 using the processing device 12 (the first display control device) so as to be distinguishable from other ranges using different colors, different types of shading, or the like without displaying the guide lines 34 and 35.

Figure 8:
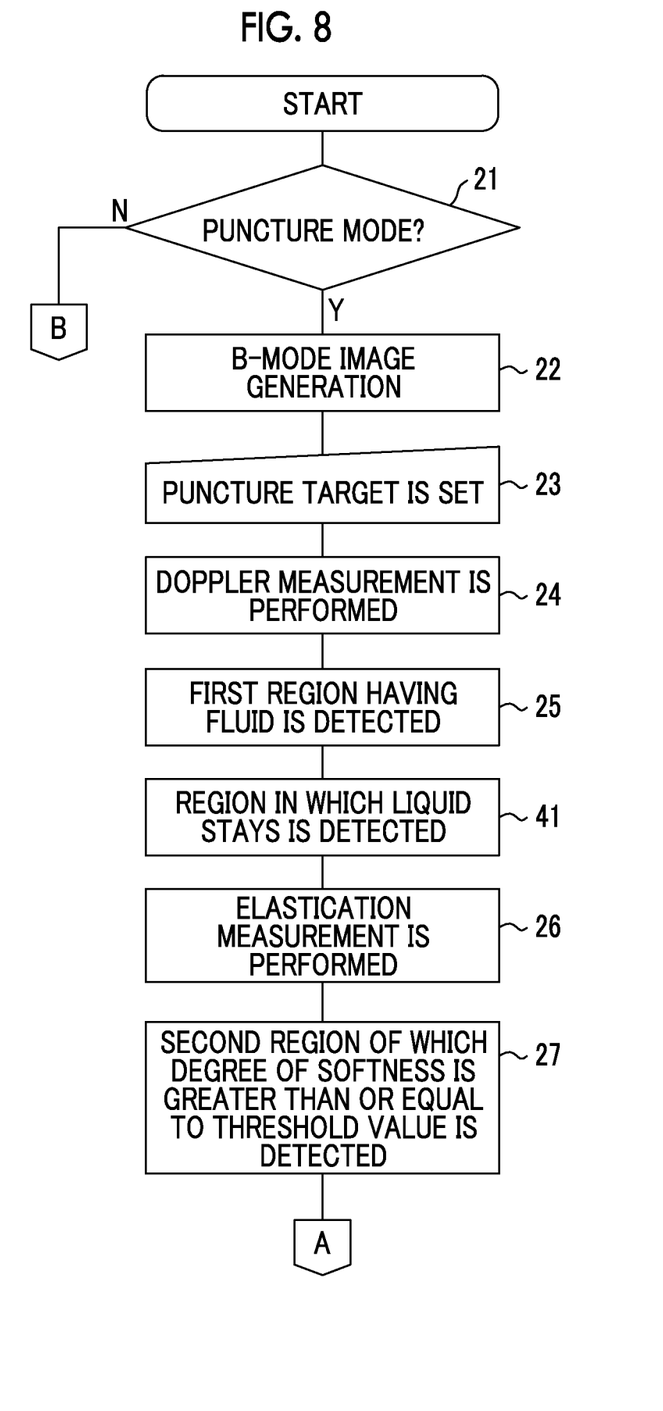
FIG. 8 is a flowchart showing a part of a processing procedure of the ultrasound diagnostic apparatus.
Figure 9:
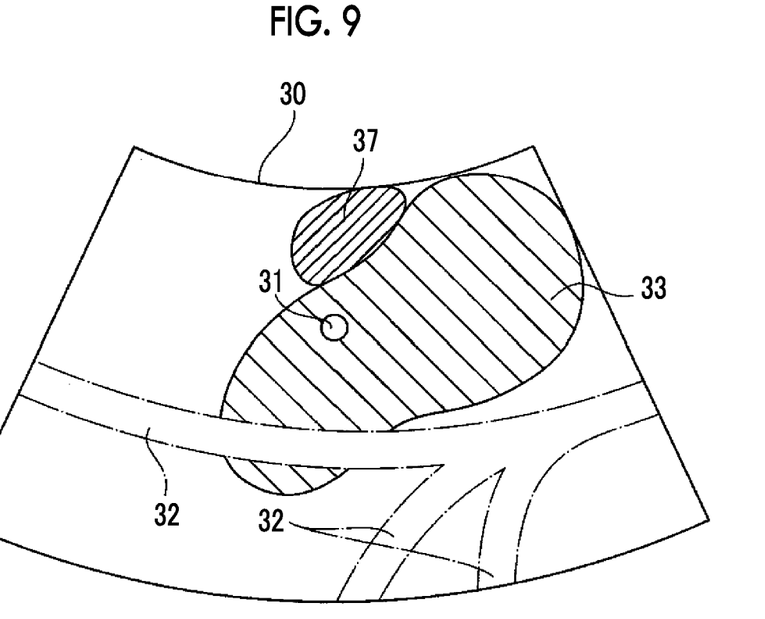
FIG. 9 is an example of an ultrasound image.
Figure 10:
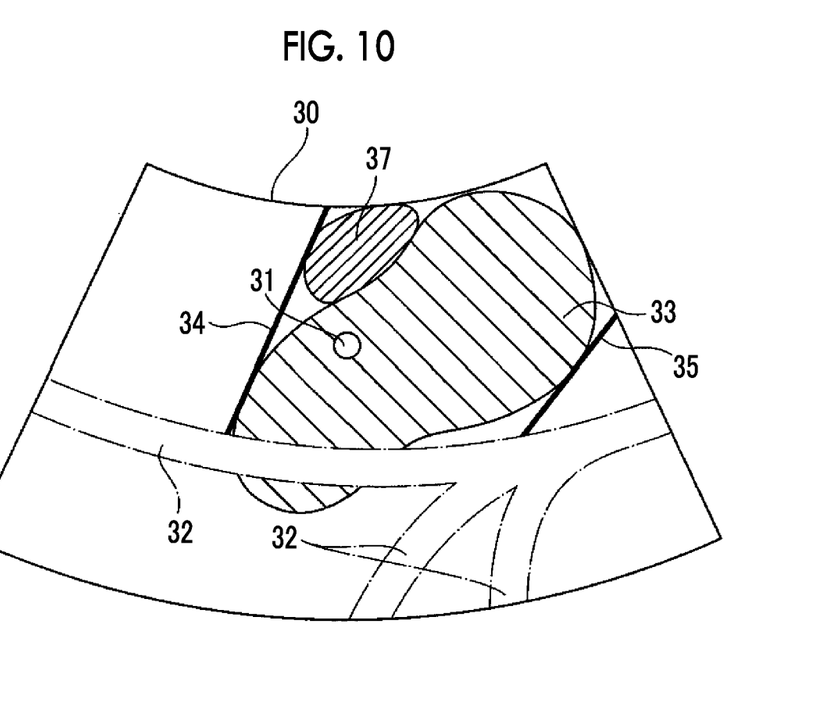
FIG. 10 is an example of an ultrasound image.

FIG. 8 is a flowchart showing a part of a processing procedure of the ultrasound diagnostic apparatus 1 and showing a modification example. The processing procedure shown in FIG. 8 corresponds to the processing procedure shown in FIG. 2. In the processing shown in FIG. 8, the same reference numerals are given to the same processing as that shown in FIG. 2. FIGS. 9 and 10 are examples of the ultrasound image 30.

As is described while referring to FIG. 2, when a puncture mode is set (YES in step 21), a B-mode image is generated (step 22), a puncture target region 31 is set (step 23), and Doppler measurement is performed (step 24), a blood stream (a first region having a fluid) 32 is detected by the control device 2 (the first detection device) (step 25) (refer to FIG. 9). In a region in which the blood stream 32 (the first region having a fluid) in the inside of the subject is excluded, a non-echo region is detected by the control device 2 (the third detection device) as a region 37 (third region) in which a liquid stays, using the ultrasound echo signal output from the ultrasound probe 6 (step 41) (refer to FIG. 9). The liquid refers to a body fluid, for example, a pancreatic fluid. The non-echo region is, for example, a region in which the ultrasound echo signal is less than or equal to a predetermined value. In other words, the non-echo region is a region which is darkened compared to a usual tissue image in the B-mode image. Thereafter, elastication processing is performed (step 26) and the soil region 33 (second region) is detected by the control device 2 (the second detection device) (step 27) (refer to FIG. 9).

At least one of a range including the soft region 33 (second region) but excluding the blood stream 32 (first region) and a range including the region 37 (third region, non-echo region) in which a liquid stays but excluding the blood stream 32 (first region) is determined as a puncture recommendation range using the control device 2 (the puncture recommendation range determination device).

Referring to FIG. 9, the region 37 in which a liquid stays in the inside of the subject is a region where there is no problem even if it is punctured with a needle, unlike the blood stream 32. For this reason, the control device 2 determines at least one of the range including the soft region 33 in which the blood stream 32 is excluded and a range including the detected region 37 in which a liquid stays and the blood stream 32 is excluded, as a puncture recommendation range.

Referring to FIG. 10, in the ultrasound image 30, the range of the soft region 33 in which the blood stream 32 (the first region having a fluid) is excluded and the region 37 in which a liquid stays is interposed between the guide lines 34 and 35 and the range interposed between these guide lines 34 and 35 is set to a puncture recommendation range. In this manner, the control device 2 (the puncture recommendation range determination device) can determine the range including the region 37 (third region), in which a liquid stays, and the soft region 33 (second region) but excluding the blood stream 32 (the first region having a fluid), as a puncture recommendation range. However, the range including the region 37 in which a liquid stays and in which the blood stream 32 (the first region having a fluid) is excluded may be set to a puncture recommendation range as described above.

Figure 11:
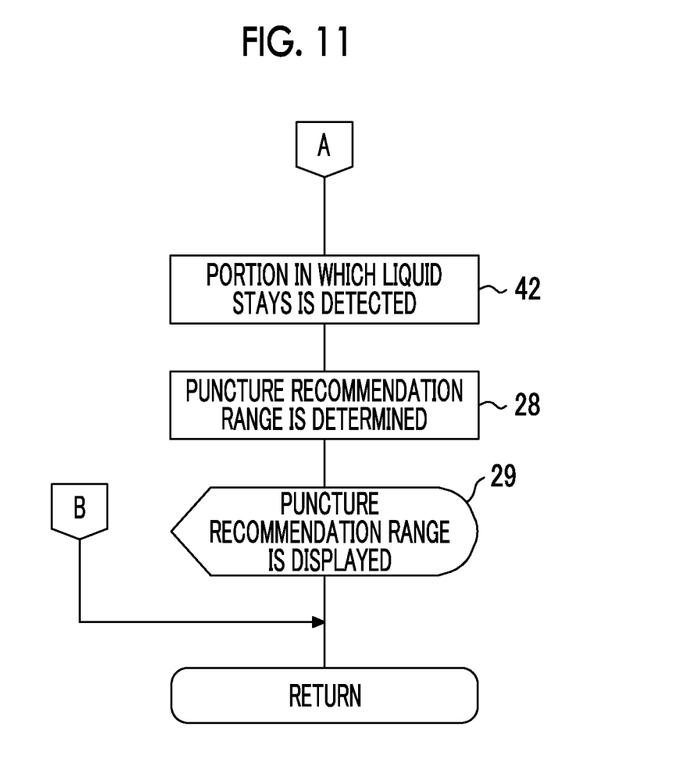
FIG. 11 is a flowchart showing a part of a processing procedure of the ultrasound diagnostic apparatus.

FIG. 11 is a flowchart showing a part of a processing procedure of the ultrasound diagnostic apparatus 1 and showing a modification example. The processing procedure shown in FIG. 11 corresponds to the processing procedure shown in FIG. 3. The same reference numerals are given to the same processing as that shown in FIG. 3, and the description thereof will not be repeated.

In the above-described example, when the blood stream 32 (the first region having a fluid) and the soft region 33 are detected, a puncture recommendation range is determined. However, in the example shown in FIG. 11, when the blood stream 32 (the first region having a fluid) and the soft region 33 are detected, a B-mode image is generated by the B-mode processing device 10 using the ultrasound echo signal output from the ultrasound probe 6. The control device 2 (the third detection device) performs image processing of detecting a non-echo region regarding a region in which both the blood stream 32 (first region) and the soft region 33 (second region) are removed, on the generated B-mode image, to detect the non-echo region as the region (third region) in which a liquid stays (step 42).

Figure 12:
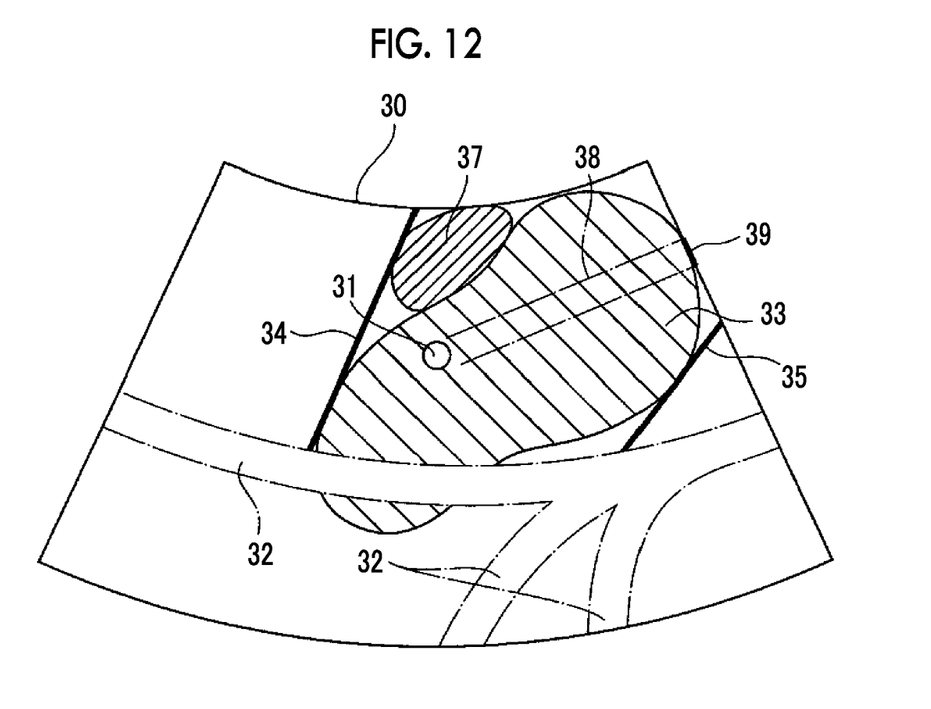
FIG. 12 is an example of an ultrasound image.

FIG. 12 is an example of an ultrasound image 30 which shows another example.

In the ultrasound image 30 shown in FIG. 12, a shortest route 38 up to the puncture target region 31 is displayed.

A needle is set to be inserted into the subject from a portion shown by a reference numeral 39. In a case where a puncture target is set by the operation device 3 (the puncture target-setting device) and the puncture target region 31 is determined, the control device 2 (the shortest route determination device) determines that a straight line from the portion shown by the reference numeral 39 to the puncture target region 31 is the shortest route 38 within the puncture recommendation range. The determined shortest route 38 is displayed on the ultrasound image 30 by the processing device 12 (the second display control device). The ultrasound image 30 on which the shortest route 38 appears is displayed on the display screen of the display device 11.

Figure 13:
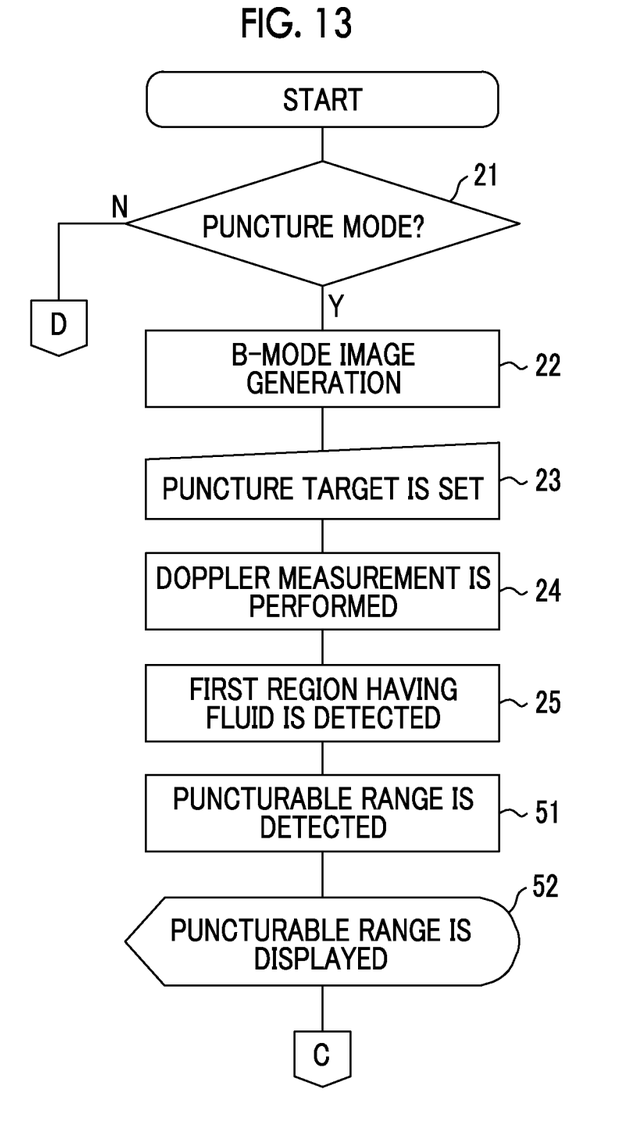
FIG. 13 is a flowchart showing a part of a processing procedure of the ultrasound diagnostic apparatus.
Figure 14:
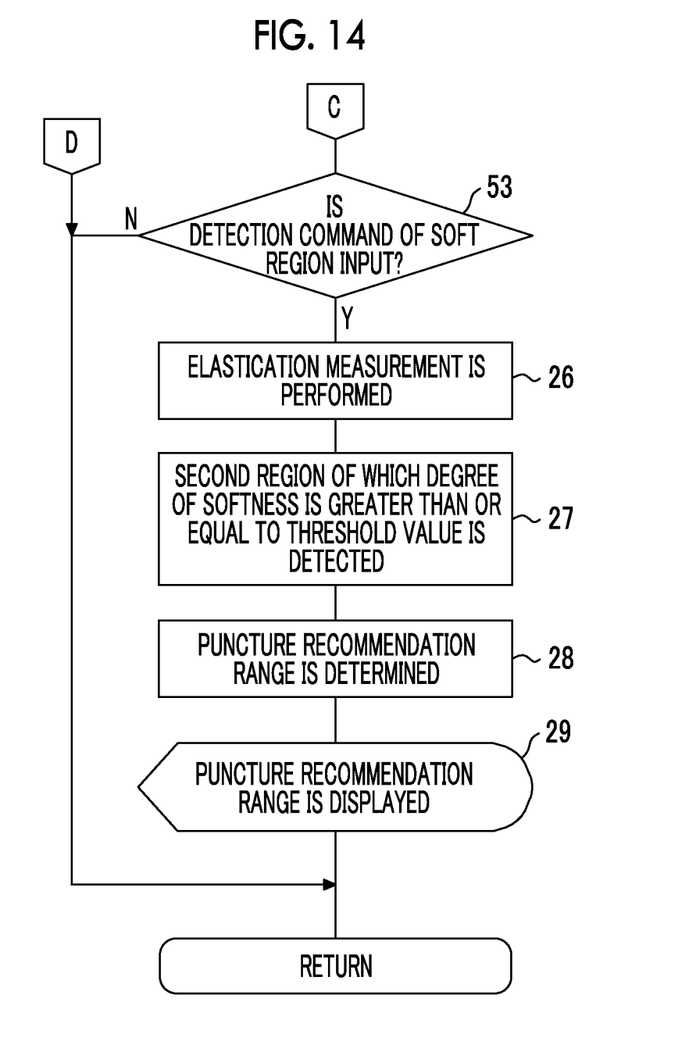
FIG. 14 is a flowchart showing a part of a processing procedure of the ultrasound diagnostic apparatus.

FIGS. 13 and 14 are flowcharts showing processing procedures of the ultrasound diagnostic apparatus 1 and showing other examples. In these drawings, the same reference numerals are given to the same processing as those shown in FIGS. 2 and 3.

As described above, when a puncture mode is set (YES in step 21), a B-mode image (acoustic wave image) in the inside of the subject is generated by the B-mode processing device 10 (the acoustic wave image generation device) using acoustic wave echo data output from the ultrasound probe 6 (step 22), a puncture target is set (step 23), and a first region having a fluid is detected through the Doppler processing (steps 24 and 25).

In these examples, when the first region having a fluid is detected, a range including a region in which the first region having a fluid is removed is determined as a puncturable range using a control device 2 before a soft region of the subject is detected through elastication processing (step 51). The determined puncturable range is displayed on the ultrasound image 30 in a superimposed manner using the processing device 12 (the third display control device) (step 52).

Figure 15:
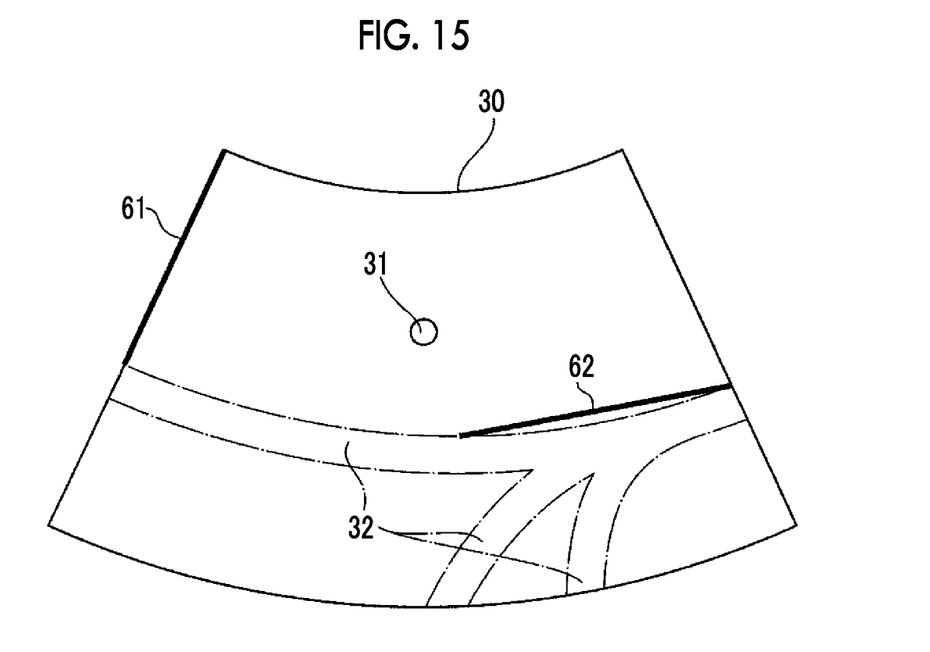
FIG. 15 is an example of an ultrasound image.

FIG. 15 is an example of an ultrasound image 30 on which a puncturable range is superimposed.

Guide lines 61 and 62 are displayed on the ultrasound image 30. The range interposed between the guide lines 61 and 62 is a puncturable range. The puncturable range is displayed on the ultrasound image 30 in a superimposed manner by displaying the guide lines 61 and 62 on the ultrasound image 30 in a superimposed manner using the processing device 12. A region in which the blood stream 32 is excluded is set to a puncturable range.

When a doctor determines that it is necessary to display a puncture recommendation range which is a range showing a region in which the first region having a fluid is excluded and a soft region using the guide lines 34 and 35 while checking the ultrasound image 30, a detection command for starting detection of the soft region (second region) using the control device 2 (the second detection device) is input from the operation device 3 (the detection command input device) (YES in step 53 in FIG. 13). Then, elastication processing is performed as described above (step 26) and the soft region (second region) of the subject is detected (step 27). The control device 2 (the second detection device) detects the soft region of the subject in response to the detection command which has been input. The soft region of the subject in which the region having a fluid is excluded in the subject is determined as a puncture recommendation range using the control device 2 (step 28) and the guide lines 34 and 35 shown in FIG. 7 are displayed on the ultrasound image 30 (step 29). The doctor performs puncturing with a needle within the puncture recommendation range specified by the guide lines 34 and 35 to puncture the puncture target region 31 with the needle.

In the above-described examples, it is preferable that the colors of the guide lines 61 and 62, the thickness of the lines, and the types of the lines showing the puncturable range are displayed differently from the colors of the guide lines 34 and 35, the thickness of the lines, and the types of the lines showing the puncture recommendation range, using the processing device 12 (the first display control device, the third display control device). In addition, it is preferable that the colors of the puncturable range specified by the guide lines 61 and 62 and the puncture recommendation range specified by the guide lines 34 and 35 are displayed differently from all of the colors of other ranges and the color of an image of a needle, using the processing device 12 (the first display control device).

In the above-described examples, the control device 2 (the second detection device) may detect a soft region from the entirety of the inside of a subject which is represented by an ultrasound echo signal output from the ultrasound probe 6. However, it is more preferable to detect the soft region (second region) by performing elastication processing on the detected region in which the first region having a fluid is excluded, as described above. This is because it is possible to reduce the calculation amount of the elastication processing.

In addition, the control device 2 (the first detection device) may detect the first region having a fluid in the inside of the subject by detecting a region in which the region having a fluid in the inside of the subject is excluded and which is represented by an ultrasound echo signal output from the ultrasound probe 6. Furthermore, a hard region which is detected by detecting a region of which the degree of hardness in the inside of the subject is less than a threshold value may be excluded using an ultrasound echo signal output from the ultrasound probe 6 to detect the excluded region as a soft region (second region) using the control device 2 (the second detection device).

Furthermore, the control device 2 (the third detection device) may detect the region 37 in which a liquid stays regarding a region excluding the detected blood stream 32 or may detect the region 37 in which a liquid stays regarding a region excluding the detected soft region 33.

What is claimed is:

1. A puncture range determination apparatus comprising:
   an acoustic wave probe which outputs an acoustic wave echo signal by transmitting an acoustic wave to a subject and receiving an acoustic wave echo from the subject;

a first detection device for detecting a first region having a fluid in the inside of the subject by performing Doppler processing using the acoustic wave echo signal output from the acoustic wave probe;

a second detection device for detecting a second region of which the degree of softness in the inside of the subject is greater than or equal to a threshold value by performing elastication processing using the acoustic wave echo signal output from the acoustic wave probe; and a puncture recommendation range determination device for determining a range which includes the second region and excludes the first region, as a puncture recommendation range.

2. The puncture range determination apparatus according to claim 1, further comprising:

a third detection device for performing processing of detecting a non-echo region as a third region on a region excluding the first region in the inside of the subject using the acoustic wave echo signal output from the acoustic wave probe, wherein the puncture recommendation range determination device determines at least one of a range including the second region but excluding the first region and a range including the third region but excluding the first region, as a puncture recommendation range.

3. The puncture range determination apparatus according to claim 2, wherein the puncture recommendation range determination device determines a range including the second region and the third region and excluding the first region, as a puncture recommendation range.

4. The puncture range determination apparatus according to claim 2, wherein the third detection device detects the third region by performing processing of detecting a non-echo region on a region excluding the first region and a region excluding the second region.

5. The puncture range determination apparatus according to claim 2, further comprising:

an acoustic wave image generation device for generating an acoustic wave image in the inside of the subject using the acoustic wave echo signal output from the acoustic wave probe, wherein the third detection device detects a region in which a liquid stays inside the subject using the acoustic wave image generated by the acoustic wave image generation device.

6. The puncture range determination apparatus according to claim 1, wherein the second detection device detects the second region by performing elastication processing on a region excluding the first region.

7. The puncture range determination apparatus according to claim 1, further comprising:

an acoustic wave image generation device for generating an acoustic wave image in the inside of the subject using the acoustic wave echo signal output from the acoustic wave probe; and a first display control device which displays the puncture recommendation range on a display screen while superimposing the puncture recommendation range on the acoustic wave image.

8. The puncture range determination apparatus according to claim 7, wherein the first display control device displays the puncture recommendation range in a color different from any of a color of the other range and a color of an image of a needle.

9. The puncture range determination apparatus according to claim 7, further comprising:

a puncture target-setting device for setting a puncture target using the acoustic wave image;

a shortest route determination device for determining a shortest route up to the puncture target in a case where the puncture target is set and the puncture recommendation range is determined; and a second display control device for displaying the shortest route on a display screen.

10. The puncture range determination apparatus according to claim 1, further comprising:

an acoustic wave image generation device for generating an acoustic wave image in the inside of the subject using the acoustic wave echo signal output from the acoustic wave probe;

a third display control device for displaying a range including a region excluding the first region on a display screen as a puncturable range while superimposing the range containing the region excluding the first region on the acoustic wave image generated by the acoustic wave image generation device; and a detection command input device for inputting a detection command for starting detection of the second region performed by the second detection device, wherein the second detection device detects the second region in a case where the detection command is input to the detection command input device.

11. The puncture range determination apparatus according to claim 1, wherein the first detection device detects the first region by detecting a region excluding a fluid in the inside of the subject using the acoustic wave echo signal output from the acoustic wave probe.

12. The puncture range determination apparatus according to claim 1, wherein the second detection device detects a region excluding a region of which the degree of hardness in the inside of the subject is less than the threshold value as the second region using the acoustic wave echo signal output from the acoustic wave probe.

13. A puncture range determination method comprising:

causing a first detection device to detect a first region having a fluid in the inside of the subject by performing Doppler processing using an acoustic wave echo signal output from an acoustic wave probe which outputs an acoustic wave echo signal by transmitting an acoustic wave to a subject and receiving an acoustic wave echo from the subject;

causing a second detection device to detect a second region of which the degree of softness in the inside of the subject is greater than or equal to a threshold value by performing elastication processing using the acoustic wave echo signal output from the acoustic wave probe; and causing a puncture recommendation range determination device to determine a range which includes the second region and excludes the first region, as a puncture recommendation range.

* * * * *